(12) United States Patent
Stehning et al.

(10) Patent No.: US 10,185,011 B2
(45) Date of Patent: Jan. 22, 2019

(54) EPT METHOD OF ELECTRIC CONDUCTIVITY RECONSTRUCTION WITH ENHANCED STABILITY AND SPEED

(71) Applicant: KONINKLIJKE PHILIPS N.V., Eindhoven (NL)

(72) Inventors: Christian Stehning, Eindhoven (NL); Ulrich Katscher, Eindhoven (NL); Thomas Heiko Stehle, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 155 days.

(21) Appl. No.: 15/302,565

(22) PCT Filed: Apr. 10, 2015

(86) PCT No.: PCT/EP2015/057856
§ 371 (c)(1),
(2) Date: Oct. 7, 2016

(87) PCT Pub. No.: WO2015/158625
PCT Pub. Date: Oct. 22, 2015

(65) Prior Publication Data
US 2017/0030988 A1  Feb. 2, 2017

(30) Foreign Application Priority Data

Apr. 16, 2014  (EP) .................................... 14164942

(51) Int. Cl.
*G01V 3/00* (2006.01)
*G01R 33/56* (2006.01)
(Continued)

(52) U.S. Cl.
CPC .......... *G01R 33/5608* (2013.01); *A61B 5/055* (2013.01); *A61B 5/0536* (2013.01); *G01R 33/246* (2013.01); *G01R 33/443* (2013.01)

(58) Field of Classification Search
CPC ...................................................... A61B 5/0536
(Continued)

(56) References Cited

U.S. PATENT DOCUMENTS 8,942,931 B2 * 1/2015 Bulumulla ........... G01R 33/246
324/309
9,638,777 B2 * 5/2017 Voigt .................... G01R 33/48
(Continued)

OTHER PUBLICATIONS

Voigt, T. et al.: "Quantitative Conductivity and Permittivity Imaging of the Human Brain Using Electric Properties Tomography", Magn. Reson. in Med., vol. 66, 2011, pp. 456-466.
(Continued)

*Primary Examiner* — Louis Arana

(57) ABSTRACT

An electric properties tomography method for reconstructing a spatial distribution of electric conductivity ($\sigma$) from magnetic resonance image data representative of a magnetic resonance image of at least a portion of a subject of interest (20), the spatial distribution covering at least a portion of the area of the magnetic resonance image, and the method comprising following steps:—segmenting the magnetic resonance image,—extrapolating acquired phase values, —replacing acquired phase values by the extrapolated phase values,—transforming into the frequency domain,—multiplying a frequency domain-transformed numerical second derivative by the acquired phase values and the frequency domain-transformed numerical second derivative by the extrapolated phase values, respectively, and—transforming the result of the multiplying into the spatial domain. Also covered are a corresponding MRI system and a software module.

19 Claims, 4 Drawing Sheets

(51) Int. Cl.
  *A61B 5/055* (2006.01)
  *G01R 33/24* (2006.01)
  *G01R 33/44* (2006.01)
  *A61B 5/053* (2006.01)

(58) Field of Classification Search
  USPC ........................................ 324/306, 307, 309
  See application file for complete search history.

(56) References Cited

U.S. PATENT DOCUMENTS

2015/0153431 A1* 6/2015 Hancu ................ G01R 33/4816
                                                              324/309
2016/0242673 A1* 8/2016 Grychtol .............. A61B 5/0536
2016/0367141 A1* 12/2016 Lee ..................... A61B 5/4875

OTHER PUBLICATIONS

Kim, Min-Oh et al.: "Phase unhanding in bSSFP for Liver conductivity imaging at 3.01",Proceedings of the International Society for Magnetic Resonance in Medicine, 21st Annual Meeting Proceedings,Apr. 20, 2013 (Apr. 20, 2013), p. 4173.

Katscher U. et al.: "Estimation of breast tumor conductivity using parabolic phase fitting",International Society for M Agnetic Resonance in Medicine, May 5, 2012 (May 5, 2012), p. 3482.

Stehning C et al., "Whole Heart Coronary MRA Using 2D Self-Navigation" Proc. Intl. Soc. Mag. Reson. Med. 19 (2011) 128.

Ecabert et al. "Automatic Model-Based Segmentation of the Heart in CT Images", IEEE Transactions on Medical Imaging, vol. 27 (9) 2008.

Katscher et al "Determination of Electric Conductivity and Local SAR Via B1 Mapping" IEEE Transactions on Medical Imaging , vol. 28, No. 9, Sep. 2009.

* cited by examiner

EPT METHOD OF ELECTRIC CONDUCTIVITY RECONSTRUCTION WITH ENHANCED STABILITY AND SPEED

CROSS REFERENCE TO RELATED APPLICATIONS

This application is a U.S. national phase application of International Application No. PCT/EP2015/057856, filed on Apr. 10, 2015, which claims the benefit of EP provisional Application Serial No. 14164942.6 filed on Apr. 16, 2014 and is incorporated herein by reference.

FIELD OF THE INVENTION

The invention pertains to an electric properties tomography (EPT) method for reconstructing a spatial distribution of electric conductivity from magnetic resonance image data representative of a magnetic resonance image of at least a portion of a subject of interest.

BACKGROUND OF THE INVENTION

In the paper by Katscher, U. et al., "*Determination of Electric Conductivity and Local SAR Via B1 Mapping*" (IEEE Trans. Med. Imag. 2009; 28:1365-1374), it has been suggested to derive electric conductivity of portions of a subject of interest from spatial sensitivity distributions of applied radio frequency coils of a magnetic resonance imaging system by an Electric Properties Tomography (EPT) approach. The electric properties of the portions of the subject of interest can potentially be used as additional information for supporting diagnostics with the object to discriminate healthy tissue from malign tissue, e.g. a tumor.

The paper by Voigt, T. et al., "*Quantitative Conductivity and Permittivity Imaging of the Human Brain Using Electric Properties Tomography*" (Magn. Reson. in Med. 2011; 66:456-466) describes a method and formula for reconstructing spatial electric conductivity distributions of portions of a subject of interest from phase images of the radio frequency transmit field employed in magnetic resonance imaging.

Katscher et al., Proc ISMRM 2012, p. 3482 describes an EPT reconstruction algorithm, based on fitting local parabolic functions on the Tx phase. The publication describes that parabola fitting can be used to remove boundary artefacts.

It is desirable to provide a fast and robust method for reconstructing a spatial distribution of electric conductivity of a portion of a subject of interest from magnetic resonance image data.

SUMMARY OF THE INVENTION

The electric conductivity $\sigma$ can be quantitatively reconstructed from a transceive phase $\varphi$, which is the superposition of a radio frequency transmit phase and a radio frequency receive phase, via $$\sigma(r) = \frac{\Delta \varphi(r)}{2\mu_0 \omega} \quad \text{eq. (1)}$$

where $\mu_0$, denotes the vacuum magnetic permeability, $\omega$ the Larmor frequency, and $\Delta = \nabla^2$ the so-called Laplace operator or Laplacian.

In a numerical approach, the calculation of the Laplacian is realized by a convolution of a differentiation kernel and the transceive phase $\varphi$ of the acquired magnetic resonance image.

The CPU processing time required for calculating the electric conductivity $\sigma$ can significantly be shortened by a Fourier transformation of the differentiation kernel and the transceive phase $\varphi$ into the frequency domain, which reduces the convolution to merely a multiplication. However, in the frequency domain, boundaries between different anatomic compartments, in particular between tissue and air, cannot be identified, leading to severe artifacts when performing the Laplacian operation across tissue boundaries.

For instance, the phase evolution between soft tissue and lipids may be uncontinuous for selected magnetic resonance imaging techniques, such as balanced Fast Field Echo (bFFE). Moreover, bone, ligament and other species may show a magnetic resonance signal close to zero and, consequently, have a very noisy magnetic resonance image signal phase.

It is therefore an object of the invention to provide a fast and robust method, based on electric properties tomography (EPT), for reconstructing a spatial distribution of electric conductivity from magnetic resonance image data which generates an as low as possible number of artifacts.

In one aspect of the present invention, the object is achieved by an electric properties tomography method for reconstructing a spatial distribution of electric conductivity from magnetic resonance image data representative of a magnetic resonance image of at least a portion of a subject of interest. The spatial distribution covers at least a portion of the area of the magnetic resonance image.

The method comprises steps of

- segmenting the magnetic resonance image into voxels corresponding to a volume of interest and voxels outside the volume of interest, wherein the voxels corresponding to the volume of interest and the voxels outside the volume of interest are separated by a segmentation boundary;
- extrapolating acquired phase values of at least the magnetic resonance image data corresponding to voxels of the volume of interest proximal to the segmentation boundary to obtain extrapolated phase values for voxels of a volume outside and adjacent the volume of interest;
- replacing acquired phase values of magnetic resonance data corresponding to voxels of the volume outside and adjacent the volume of interest by the extrapolated phase values;
- transforming into the frequency domain a numerical kernel representing a numerical second derivative, the acquired phase values corresponding to the voxels of the volume of interest, and the extrapolated phase values corresponding to the voxels outside and adjacent the volume of interest;
- multiplying the frequency domain-transformed numerical second derivative by the acquired phase values and the frequency domain-transformed numerical second derivative by the extrapolated phase values, respectively; and
- transforming the result of the step of multiplying into the spatial domain.

In this way, boundary artifacts can be reduced or avoided that might be generated if the numerical kernel representing a numerical second derivative is applied to voxels of significantly different electric conductivity.

Thus, the method is highly effective in particular in cases wherein the magnetic resonance image data are representative of a magnetic resonance image comprising one out of head, liver, kidney and prostate of the subject of interest.

In one embodiment, the volume outside and adjacent the volume of interest may comprise at least five voxels in two linearly independent directions, more preferably at least ten voxels, and, most preferably, at least 20 voxels in two linearly independent directions.

Preferably, the extrapolated phase values are selected to be constant. By that, large steps in phase of the voxels of the volume of interest proximal to the segmentation boundary and of the voxels outside and adjacent the volume of interest can readily be avoided.

In a preferred embodiment of the method, the step of extrapolation includes a three-dimensional parabolic extrapolation of phase values. In this way, the extrapolated phase values can readily be calculated.

In another preferred embodiment of the method, the step of segmenting is carried out employing a model-based segmentation approach. By that, a model shape of the portion of the subject of interest can be adapted parametrically to match an anatomic detail of the portion of the subject of interest for obtaining a most accurate segmentation, and a more precise spatial distribution of the electric conductivity can be achieved. A surface of the model may be represented in a faceted mode, drawn as a series of planar regions like rectangles or triangles that approximates the surface of the anatomic detail. In general, in the surface representation the surface may be represented in any other mode that appears suitable to the one skilled in the art, for instance a wire frame representation.

In yet another preferred embodiment, the method comprises a step of filtering in the spatial domain, wherein the step is carried out after the step of transforming the result of the step of multiplying into the spatial domain, for accomplishing noise reduction.

In another aspect of the invention, a magnetic resonance imaging system configured for acquiring magnetic resonance images of at least a portion of a subject of interest is provided. The magnetic resonance imaging system comprises:
- an examination space provided to position at least the portion of the subject of interest within;
- a main magnet configured for generating a static magnetic field $B_0$ in the examination space;
- a magnetic gradient coil system configured for generating gradient magnetic fields superimposed to the static magnetic field $B_0$;
- at least one radio frequency antenna device that is configured for applying a radio frequency excitation field $B_1$ to nuclei of or within the portion of the subject of interest for magnetic resonance excitation,
- at least one radio frequency antenna device that is configured for receiving magnetic resonance signals from the nuclei of or within the portion of the subject of interest that have been excited by applying the radio frequency excitation field $B_1$;
- a control unit configured for controlling functions of the magnetic resonance imaging system; and
- a processor unit configured to carry out steps of an embodiment of any of the methods disclosed herein or a combination thereof.

Preferably, the control unit of the magnetic resonance imaging system is configured to initiate pulse sequences, wherein each pulse sequence is configured to generate radio frequency fields via the at least one radio frequency antenna device and magnetic gradient fields via the magnetic gradient coil system. The pulse sequences are insensitive to variations of the static magnetic field $B_0$.

In one embodiment, the control unit may be configured to initiate pulse sequences suitable for at least one of
- balanced gradient steady-state free precession (bSSFP) sequences, in particular a three-dimensional balanced Fast Field Echo (3D-bFFE) sequence, and
- three-dimensional spin echo sequences, in particular a three-dimensional Turbo Spin Echo (3D-TSE) sequence.

In yet another aspect of the present invention, a software module is provided for carrying out an embodiment of any one of the methods disclosed above or a combination thereof, of reconstructing a spatial distribution of electrical conductivity from magnetic resonance image data representative of a magnetic resonance image of at least a portion of a subject of interest. The method steps to be conducted are converted into a program code of the software module, wherein the program code is implementable in a memory unit of the magnetic resonance imaging system and is executable by a processor unit of the magnetic resonance imaging system. The processor unit may be the processor unit of the control unit that is customary for controlling functions of a magnetic resonance imaging system. The processor unit may, alternatively or supplementary, be another processor unit that is especially assigned to execute at least some of the method steps.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
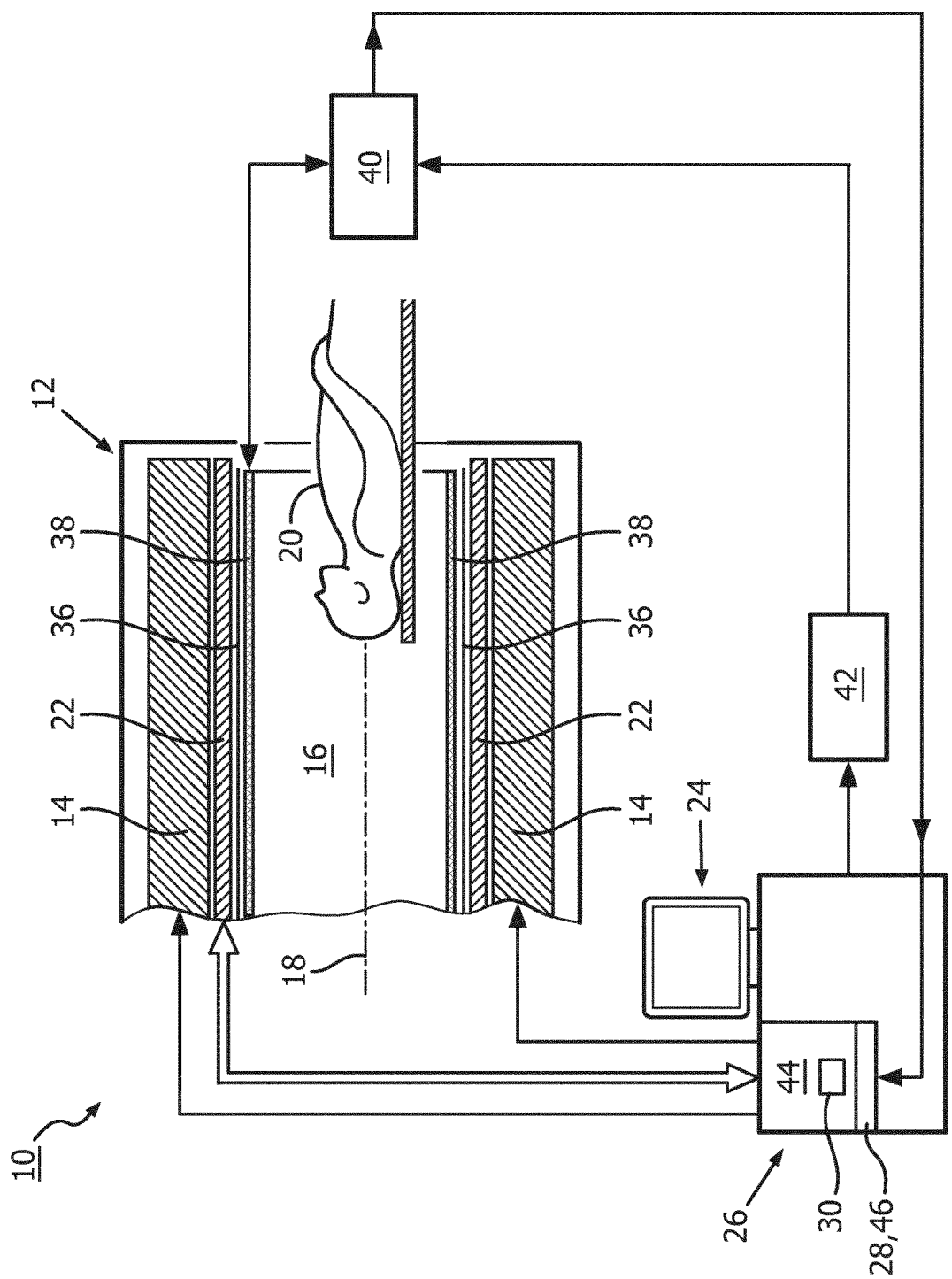
FIG. 1 shows a schematic illustration of a part of an embodiment of a magnetic resonance imaging system in accordance with the invention.

FIG. 1 shows a schematic illustration of a part of an embodiment of a magnetic resonance imaging system 10 configured for acquiring magnetic resonance images of at least a portion of a subject of interest 20, usually a patient. The magnetic resonance imaging system 10 comprises a scanning unit 12 having a main magnet 14. The main magnet 14 has a central bore that provides an examination space 16 around a center axis 18 for the subject of interest 20 to be positioned within, and is further provided for generating a static magnetic field $B_0$ at least in the examination space 16. The static magnetic field $B_0$ defines an axial direction of the examination space 16, aligned in parallel to the center axis 18. It is appreciated that the invention is also applicable to any other type of magnetic resonance imaging systems providing an examination region within a static magnetic field.

Further, the magnetic resonance imaging system 10 comprises a magnetic gradient coil system 22 configured for generating gradient magnetic fields superimposed to the static magnetic field $B_0$. The magnetic gradient coil system 22 is concentrically arranged within the bore of the main magnet 14.

The magnetic resonance imaging system 10 comprises a control unit 26 configured to control functions of the magnetic resonance imaging system 10. The control unit 26 includes a human interface device 24 including a monitor unit having a touch-sensitive screen.

Furthermore, the magnetic resonance imaging system 10 includes a radio frequency antenna device 38 designed as a whole-body coil that is provided for applying a radio frequency excitation field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter 42 to the whole-body coil. The whole-body coil has a center axis and, in the operational state, is arranged concentrically within the bore of the main magnet 14 such that the center axis of the whole-body coil and the center axis 18 of the scanning unit 12 coincide. As is well known in the art, a cylindrical metal radio frequency shield 36 is arranged concentrically between the magnetic gradient coil system 22 and the whole-body coil.

The whole-body coil is also provided for receiving magnetic resonance signals during radio frequency receive phases from the nuclei of or within the portion of the subject of interest 20 that have been excited by the transmitted radio frequency field $B_1$. In an operational state of the magnetic resonance imaging system 10, radio frequency transmit phases and radio frequency receive phases are taking place in a consecutive manner.

The radio frequency transmitter unit 42 is configured, initiated and controlled by the control unit 26, to feed radio frequency power of a magnetic resonance radio frequency and in the form, among others, of three-dimensional balanced Fast Field Echo (3D-bFFE) sequence radio frequency pulse sequences to the whole-body coil and the magnetic gradient coil system 22 via a radio frequency switching unit 40 during the radio frequency transmit phases. Each pulse sequence is configured to generate the radio frequency field $B_1$ via the radio frequency antenna device 38 and magnetic gradient fields via the magnetic gradient coil system 22, wherein the pulse sequences are relatively insensitive to variations of the static magnetic field $B_0$.

Figures 3A, 3B:
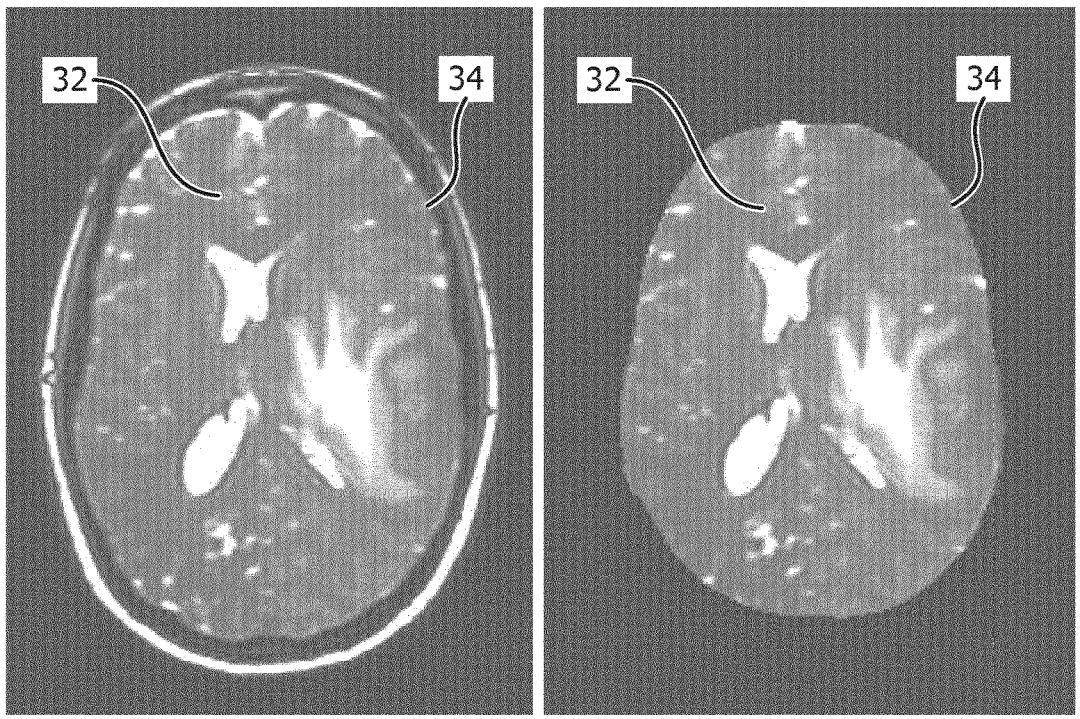
FIGS. 3(a) to 3(h) illustrate an example of applying an embodiment of a method in accordance with the invention to a magnetic resonance image of the head of a subject of interest.
Figures 3C, 3D:
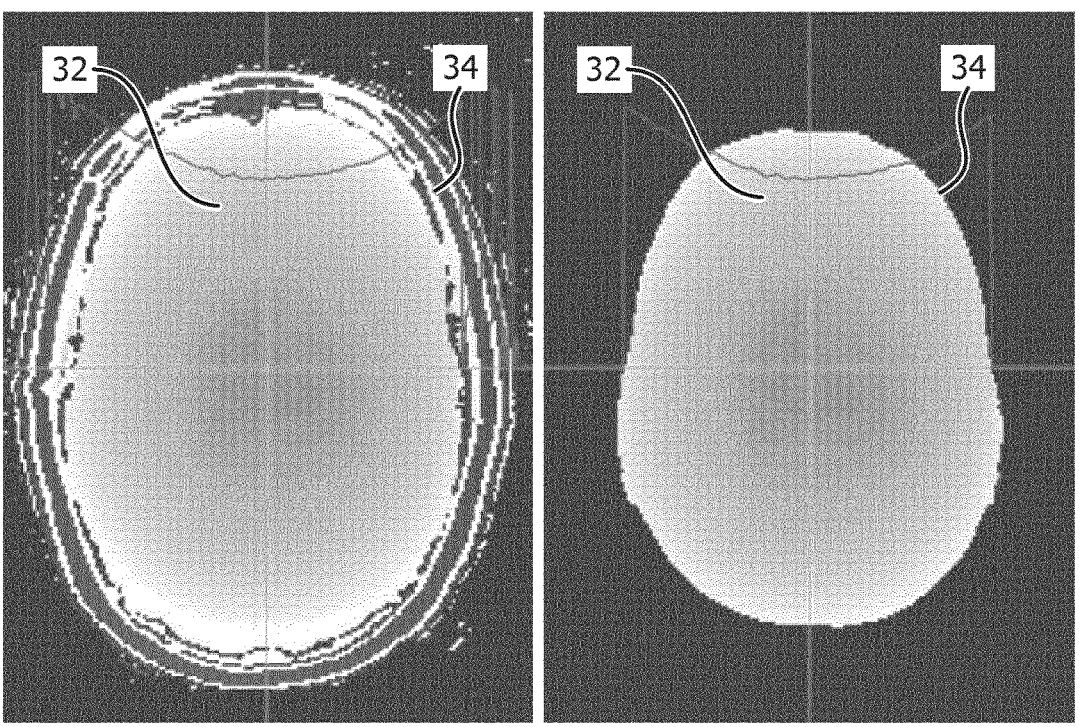

During the radio frequency receive phases, the radio frequency switching unit 40, controlled by the control unit 26, directs the magnetic resonance signals from the whole-body coil to a signal processing unit 44 residing in the control unit 26. The signal processing unit 44 is configured for processing acquired magnetic resonance signals to obtain magnetic resonance image data representative of magnetic resonance images of slices of at least the portion of the subject of interest 20, namely the head. An exemplary result obtained from the 3D-bFFE scan of the head of the subject of interest 20 is illustrated in FIGS. 3(a) and 3(c). FIG. 3(a) shows a magnitude image of a transverse slice, FIG. 3(c) illustrates a signal phase image of the transverse slice of the whole head of the subject of interest 20.

Figure 2:
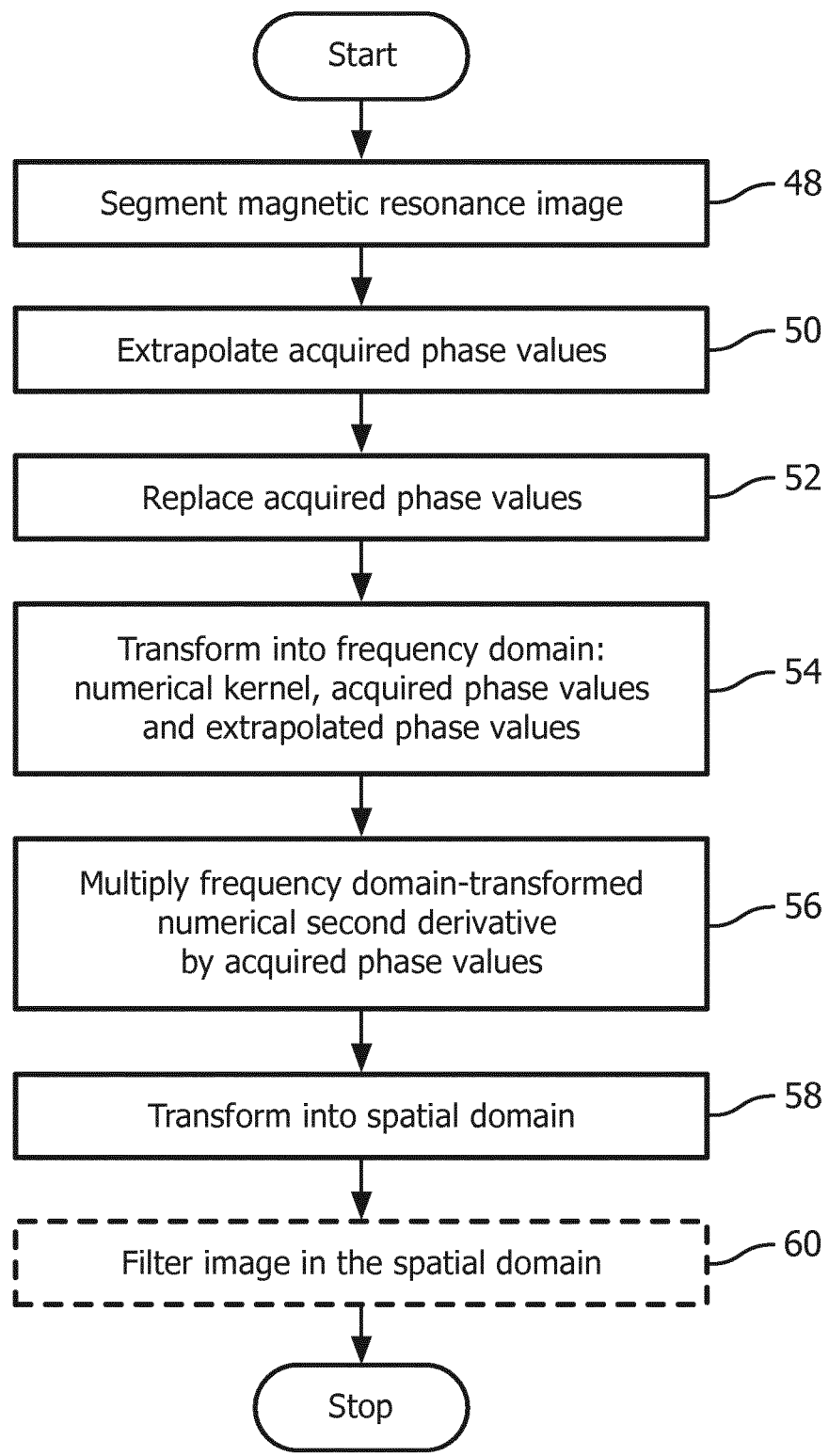
FIG. 2 is a flowchart of an embodiment of a method in accordance with the invention.

In the following, an embodiment of an electric properties tomography method for reconstructing a spatial distribution of electric conductivity σ from magnetic resonance image data representative of a magnetic resonance image of at least a portion of a subject of interest 20 is described. A principal flow chart of the method is given in FIG. 2. In preparation of conducting the method, it shall be understood that all involved units and devices are in an operational state and configured as illustrated in FIG. 1.

In order to be able to carry out the method as a specific operation of the magnetic resonance imaging system 10, the control unit 26 comprises a software module 46 (FIG. 1). The method steps to be conducted are converted into a program code of the software module 46, wherein the program code is implementable in a memory unit 28 of the control unit 26 and is executable by a processor unit 30 of the control unit 26.

The method starts from the magnetic resonance image of the transverse slice of the whole head of the subject of interest 20 as illustrated in FIGS. 3(a) and 3(c).

In a first step 48 of the method, a head model-based segmentation approach is applied for segmenting the magnetic resonance image into voxels corresponding to a volume of interest 32 and voxels outside the volume of interest 32, wherein the voxels corresponding to the volume of interest 32 and the voxels outside the volume of interest 32 are separated by a segmentation boundary 34. FIGS. 3(b) and (d) illustrate a magnitude image and a phase image, respectively, of the transverse slide of the head of the subject of interest 20, confined to the volume of interest 32 inside the segmentation boundary 34.

Image segmentation algorithms are commercially available nowadays, e.g. as a software module within MATLAB®, and shall therefore not be described in more detail herein. The phrase "segmentation algorithm", as used in this application, shall particularly encompass but shall not be limited to segmentation methods that are based on thresholding, clustering, compression, edge detection, and histogram methods. In principle, any segmentation algorithm that appears to be suitable to the one skilled in the art may be employed.

In another step 50 of the method, for all acquired phases of the voxels corresponding to the volume of interest 32, nine parameters of a three-dimensional parabolic function $\varphi_{fit}$ (r) are determined such that the three-dimensional parabolic function $\varphi_{fit}$ (r) approximates the measured phases $\varphi_{meas}$ (r) in the sense of a least squares approach (r denotes the position vector):

$$\varphi_{fit}(r) = a_0 + a_1 x + a_2 x^2 + a_3 y + a_4 y^2 + a_5 z + a_6 z^2 + a_7 xy + a_8 xz + a_9 yz + \qquad \text{eq. (2)}$$

Based on the approximation of eq. (2), acquired phase values of at least the magnetic resonance image data corresponding to voxels of the volume of interest 32 proximal to the segmentation boundary 34 are extrapolated to obtain extrapolated phase values for a specified volume outside and adjacent the volume of interest 32. In a subsequent step (52), acquired phase values of magnetic resonance data corresponding to voxels of the volume outside and adjacent the volume of interest 32 are replaced by the extrapolated phase values.

Figure 3E:
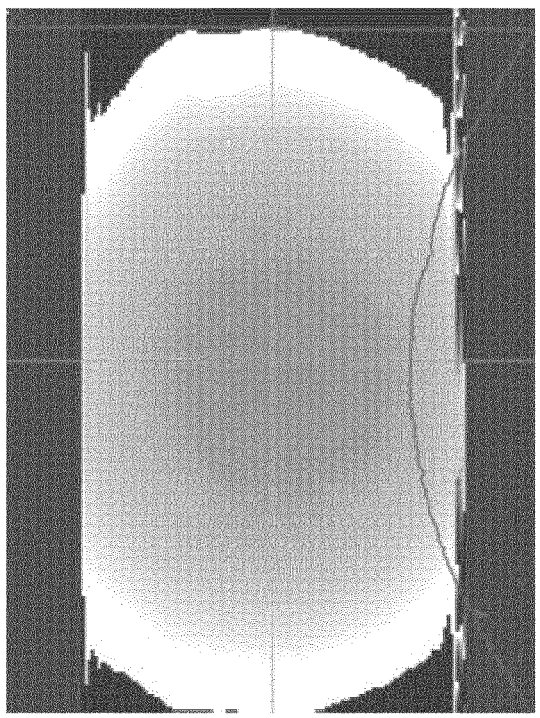
Figure 3F:
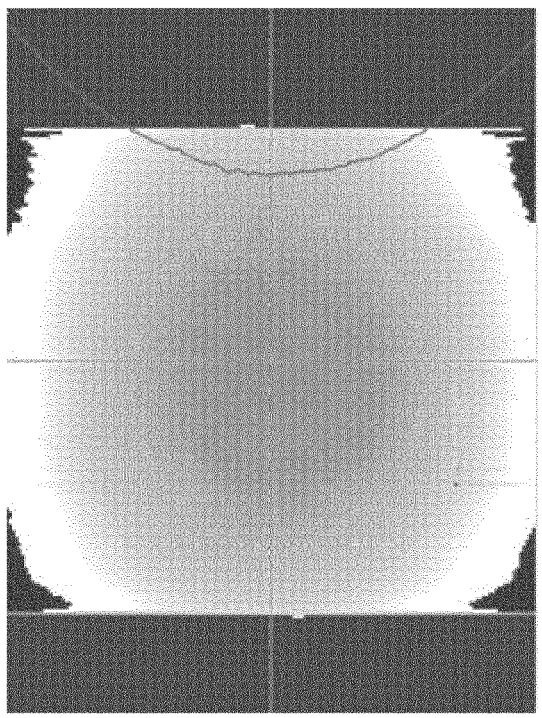

This is illustrated in FIGS. 3(e) and 3(f). FIG. 3(e) shows an extrapolation in the anterior-posterior direction, and FIG. 3(f) shows an extrapolation in the right-left direction.

In the next step 54 then, a numerical kernel representing a numerical second derivative, the acquired phase values corresponding to the voxels of the volume of interest 32, and the extrapolated phase values corresponding to the voxels outside and adjacent the volume of interest 32 are transformed into the frequency domain. The numerical kernel representing a numerical second derivative may be defined in the spatial domain for instance by the set K={1, −2, 1}.

In a following step 56, the frequency domain-transformed numerical second derivative is multiplied by the acquired phase values, and the frequency domain-transformed numerical second derivative is multiplied by the extrapolated phase values, respectively. As is appreciated by the one skilled in the art, this multiplication requires much less CPU time than a corresponding convolution of phase and differentiation kernel in the spatial domain.

In a final step 58 of this embodiment of the method, the result of the step of multiplying 56 is transformed into the spatial domain. The spatial distribution of electric conductivity σ reconstructed in this way, covering a portion of the area of the original magnetic resonance image, is shown in FIG. 3(h). As an additional option, to be carried out after the step 58 of transforming the result of the step 56 of multiplying, a step 60 of filtering the magnetic resonance image data in the spatial domain may be carried out if required.

Figure 3G:
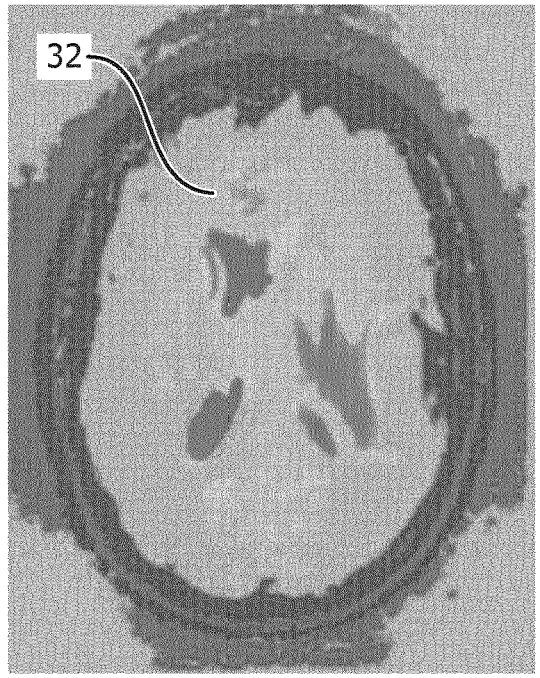
Figure 3H:

For comparison, an alternative reconstruction of a spatial distribution of electric conductivity σ from the same magnetic resonance image data by employing a prior art method is displayed in FIG. 3(g), showing that artifacts of drops in electric conductivity σ along the rim of the brain have been eliminated by employing the embodiment of the method in accordance with the invention.

It is obvious to the one skilled in the art that, although exemplarily described for the head of the subject of interest 20, the method is also applicable to magnetic resonance image data that are representative of a magnetic resonance image comprising other portions of a subject of interest 20, such as the liver, the kidney, or the prostate.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 10 magnetic resonance imaging $B_0$ static magnetic field system
12 scanning unit $B_1$ radio frequency excitation field
14 main magnet φ signal phase
16 examination space σ electric conductivity
18 center axis
20 subject of interest
22 magnetic gradient coil system
24 human interface device
26 control unit
28 memory unit
30 processor unit
32 volume of interest
34 segmentation boundary
36 radio frequency shield
38 radio frequency antenna device
40 radio frequency switching unit
42 radio frequency transmitter
44 signal processing unit
46 software module
48 step of segmenting
50 step of extrapolating phase values
52 step of replacing
54 step of transforming into frequency domain
56 step of multiplying
58 step of transforming into spatial domain
60 step of filtering

The invention claimed is:

1. An electric properties tomography method for reconstructing a spatial distribution of electric conductivity (σ) from magnetic resonance image data representative of a magnetic resonance image of at least a portion of a subject of interest, the spatial distribution covering at least a portion of the area of the magnetic resonance image, and the method comprising:

segmenting the magnetic resonance image into voxels corresponding to a volume of interest and voxels outside the volume of interest, wherein the voxels corresponding to the volume of interest and the voxels outside the volume of interest are separated by a segmentation boundary;

extrapolating acquired phase values of at least the magnetic resonance image data corresponding to voxels of the volume of interest proximal to the segmentation boundary to obtain extrapolated phase values for voxels of a volume outside and adjacent the volume of interest;

replacing acquired phase values of magnetic resonance data corresponding to voxels of the volume outside and adjacent the volume of interest by the extrapolated phase values;

transforming into the frequency domain a numerical kernel representing a numerical second derivative, the acquired phase values corresponding to the voxels of the volume of interest, and the extrapolated phase values corresponding to the voxels outside and adjacent the volume of interest;

multiplying the frequency domain-transformed numerical second derivative by the frequency domain-transformed acquired phase values and the frequency domain-transformed numerical second derivative by the frequency domain-transformed extrapolated phase values, respectively; and transforming the result of multiplying into the spatial domain.

2. The method as claimed in claim 1, wherein the extrapolated phase values are selected to be constant.

3. The method as claimed in claim 1, wherein the extrapolation includes a three-dimensional parabolic extrapolation.

4. The method as claimed in claim 1, wherein the segmenting is carried out employing a model-based segmentation approach.

5. The method as claimed in claim 1, further comprising filtering in the spatial domain, wherein the filtering is carried out after the transforming the result of the multiplying into the spatial domain.

6. The method as claimed in claim 1, wherein the magnetic resonance image data are representative of a magnetic resonance image comprising one out of head, liver, kidney and prostate of the subject of interest.

7. A magnetic resonance imaging system configured for acquiring magnetic resonance images of at least a portion of a subject of interest, comprising:
- an examination space provided to position at least the portion of the subject of interest within;
- a scanning unit having a main magnet configured for generating a static magnetic field $B_0$ in the examination space;
- a magnetic gradient coil system configured for generating gradient magnetic fields superimposed to the static magnetic field $B_0$;
- at least one radio frequency antenna device that is configured for applying a radio frequency excitation field $B_1$ to nuclei of or within the portion of the subject of interest for magnetic resonance excitation,
- at least one radio frequency antenna device that is configured for receiving magnetic resonance signals from the nuclei of or within the portion of the subject of interest that have been excited by applying the radio frequency excitation field $B_1$;
- a control unit configured for controlling functions of the magnetic resonance imaging system; and
- a processor unit configured to execute instructions to perform an electric properties tomography method for reconstructing a spatial distribution of electric conductivity from magnetic resonance image data representative of the magnetic resonance image of at least a portion of a subject of interest, the spatial distribution covering at least a portion of the area of the magnetic resonance image, the method including:
- segmenting the magnetic resonance image into voxels corresponding to a volume of interest and voxels outside the volume of interest, wherein the voxels corresponding to the volume of interest and the voxels outside the volume of interest are separated by a segmentation boundary;
- extrapolating acquired phase values of at least the magnetic resonance image data corresponding to voxels of the volume of interest proximal to the segmentation boundary to obtain extrapolated phase values for voxels of a volume outside and adjacent the volume of interest;
- replacing acquired phase values of magnetic resonance data corresponding to voxels of the volume outside and adjacent the volume of interest by the extrapolated phase values;
- transforming into the frequency domain a numerical kernel representing a numerical second derivative, the acquired phase values corresponding to the voxels of the volume of interest, and the extrapolated phase values corresponding to the voxels outside and adjacent the volume of interest;
- multiplying the frequency domain-transformed numerical second derivative by the frequency domain-transformed acquired phase values and the frequency domain-transformed numerical second derivative by the frequency domain-transformed extrapolated phase values, respectively; and
- transforming the result of multiplying into the spatial domain.

8. The magnetic resonance imaging system of claim 7, wherein the control unit is configured to initiate pulse sequences, wherein each pulse sequence is configured to generate radio frequency fields via the at least one radio frequency antenna device and magnetic gradient fields via the magnetic gradient coil system, and wherein the pulse sequences are insensitive to variations of the static magnetic field $B_0$.

9. The magnetic resonance imaging system of claim 7, wherein the extrapolated phase values are selected to be constant.

10. The method of claim 7, wherein the extrapolation includes a three-dimensional parabolic extrapolation.

11. The magnetic resonance imaging system of claim 7, wherein the segmenting is carried out employing a model-based segmentation approach.

12. The magnetic resonance imaging system of claim 7, further comprising filtering in the spatial domain, wherein the filtering is carried out after the transforming the result of the multiplying into the spatial domain.

13. The magnetic resonance imaging system of claim 7, wherein the magnetic resonance image data are representative of a magnetic resonance image comprising one out of head, liver, kidney and prostate of the subject of interest.

14. A non-transitory computer-readable storage medium configured to store executable instructions for causing one or more processors to perform an electric properties tomography method for reconstructing a spatial distribution of electric conductivity from magnetic resonance image data representative of a magnetic resonance image of at least a portion of a subject of interest, the spatial distribution covering at least a portion of the area of the magnetic resonance image, and the method comprising:
- segmenting the magnetic resonance image into voxels corresponding to a volume of interest and voxels outside the volume of interest, wherein the voxels corresponding to the volume of interest and the voxels outside the volume of interest are separated by a segmentation boundary;
- extrapolating acquired phase values of at least the magnetic resonance image data corresponding to voxels of the volume of interest proximal to the segmentation boundary to obtain extrapolated phase values for voxels of a volume outside and adjacent the volume of interest;
- replacing acquired phase values of magnetic resonance data corresponding to voxels of the volume outside and adjacent the volume of interest by the extrapolated phase values;
- transforming into the frequency domain a numerical kernel representing a numerical second derivative, the acquired phase values corresponding to the voxels of the volume of interest, and the extrapolated phase values corresponding to the voxels outside and adjacent the volume of interest;
- multiplying the frequency domain-transformed numerical second derivative by the frequency domain-transformed acquired phase values and the frequency domain-transformed numerical second derivative by the frequency domain-transformed extrapolated phase values, respectively; and
- transforming the result of multiplying into the spatial domain.

15. The non-transitory computer-readable storage medium of claim 14, wherein the extrapolated phase values are selected to be constant.

16. The non-transitory computer-readable storage medium of claim 14, wherein the extrapolation includes a three-dimensional parabolic extrapolation.

17. The non-transitory computer-readable storage medium of claim 14, wherein the segmenting is carried out employing a model-based segmentation approach.

18. The non-transitory computer readable medium of claim 14, further comprising filtering in the spatial domain, wherein the filtering is carried out after the transforming the result of the multiplying into the spatial domain.

19. The non-transitory computer readable medium of claim 14, wherein the magnetic resonance image data are representative of a magnetic resonance image comprising one out of head, liver, kidney and prostate of the subject of interest.

* * * * *